United States Patent [19]

Hagen et al.

[11] Patent Number: 4,873,386

[45] Date of Patent: Oct. 10, 1989

[54] SELECTIVE PRODUCTION OF 2,6-DIETHYLNAPHTHALENE

[75] Inventors: Gary P. Hagen, Glen Ellyn; Thomas E. Nemo, Naperville, both of Ill.

[73] Assignee: Amoco Corporation, Chicago, Ill.

[21] Appl. No.: 212,518

[22] Filed: Jun. 28, 1988

[51] Int. Cl.$^4$ .................................................. C07C 5/22
[52] U.S. Cl. .................... 585/471; 585/472; 585/474
[58] Field of Search ................ 585/471, 472, 474

[56] References Cited

U.S. PATENT DOCUMENTS

| | | | |
|---|---|---|---|
| 2,739,991 | 3/1956 | Hervert | 585/470 |
| 2,837,583 | 6/1958 | Lien et al. | 585/472 |
| 4,288,646 | 9/1981 | Olah | 585/471 |

*Primary Examiner*—Curtis R. Davis
*Attorney, Agent, or Firm*—James R. Henes; William H. Magidson; Ralph C. Medhurst

[57] ABSTRACT

A method for the highly selective production of 2,6-diethylnaphthalene involving the use of a specific Lewis acid catalyst and a highly regiospecific ethylating agent.

11 Claims, No Drawings

SELECTIVE PRODUCTION OF 2,6-DIETHYLNAPHTHALENE

BACKGROUND OF THE INVENTION

1. Field of the Invention

This invention relates to the production of a diethylnaphthalene and more particularly concerns the highly selective production of 2,6-diethylnaphthalene by the transethylation of naphthalene or 2-ethylnaphthalene by 1,4-diethylbenzene, 1,2,4-triethylbenzene, at least one tetraethylbenzene or pentaethylbenzene.

2. Description of the Prior Art

Naphthalene dicarboxylic acids are monomers that are known to be useful for the preparation of a variety of polymers. For example, poly(ethylene 2,6-naphthalate) prepared from 2,6-naphthalene dicarboxylic acid and ethylene glycol has better heat resistance and mechanical properties than polyethylene terephthalate and is useful in the manufacture of films and fibers.

Diethylnaphthalenes are desirable feedstocks for oxidation to the corresponding naphthalene dicarboxylic acids. A known conventional process for producing a naphthalene dicarboxylic acid comprises the oxidation of a diethylnaphthalene with oxygen in the liquid phase in an acetic acid solvent at an elevated temperature and pressure and in the presence of a catalyst comprising cobalt, manganese and bromine components.

Diethylnaphthalenes can be found in low concentrations in refinery streams as mixtures of some or all of the ten possible diethylnaphthalene isomers. However, separation of these isomers is very difficult and expensive. Consequently, methods for producing specific diethylnaphthalenes or mixtures of two or three specific diethylnaphthalenes in high purity and quality are highly desirable. One such method is disclosed in Japanese Kokai Patent Application Publication No. 61-83137 (Apr. 26, 1986) and is a synthesis involving the transalkylation of naphthalene or a 2-methylnaphthalene in the presence of an aluminum chloride catalyst at 0°–35° C. in the liquid phase to produce a 2,6-dialkylnaphthalene. Suitable alkylating agents are disclosed as including durene, diethylbenzene, triethylbenzene, triisopropylbenzene and isopropylxylene dibutylbenzene. The reported results indicate a relatively low degree of selectivity for the formation of specific dialkylnaphthalenes.

Japanese Kokai Patent Application Publication No. 62-252733 (Nov. 4, 1987) discloses a process for the transethylation of biphenyl with an ethylbenzene to form monoethylbiphenyl and diethylbiphenyl in the presence of a Friedel-Crafts catalyst, such as aluminum chloride, at 70°–150° C. The Japanese patent discloses that reaction temperatures of less than 70° C. delay the reaction rate. The ring positions of the ethyl substituents in the ethylated biphenyl products are not disclosed. Suitable ethylbenzenes include ethylbenzene, diethylbenzene, triethylbenzene, tetraethylbenzene, other ethyl-substituted benzenes, ethyltoluene, diethyltoluene and other ethyl-substituted toluenes. Polyethylbenzenes containing relatively small amounts of monoethylbenzene, triethylbenzene and tetraethylbenzene can also be used advantageously.

Shimada et al., "Ethylation and Transethylation of Naphthalene," Bulletin of the Chemical Society of Japan, Vol. 48 (II), pages 3306–3308 (November, 1975) disclose the transethylation of naphthalene by ethylbenzene or ethylxylenes to form monoethylnaphthalenes in the presence of an aluminum chloride catalyst at 20°–30° C. The rates of transethylation with ethylxylene isomers were reported to decrease in the order of 1,2-dimethyl-4-ethylbenzene $\geq$, 1,3-dimethyl-4-ethylbenzene $\geq$, 1,4-dimethyl-2-ethylbenzene $\geq$ 1,3-dimethyl-5-ethylbenzene.

Thus, no existing method is known for the highly selective production of 2,6-diethylnaphthalene or a mixture of 2,6- and 2,7-diethylnaphthalene by a transethylation process.

OBJECTS OF THE INVENTION

It is therefore a general object of the present invention to provide an improved method for the highly selective production of 2,6-diethylnaphthalene or a mixture of 2,6- and 2,7-diethylnaphthalene.

More specifically, it is an object of the present invention to provide an improved method for the highly selective production of 2,6-diethylnaphthalene or a mixture of 2,6- and 2,7-diethylnaphthalene by transethylating naphthalene or 2-ethylnaphthalene under highly regeospecific conditions.

Other objects and advantages of the invention will become apparent upon reading the following detailed description and appended claims and upon reference to the accompanying drawings.

SUMMARY OF THE INVENTION

These objects are achieved by an improved method for producing 2,6-diethylnaphthalene, comprising: reacting in the liquid phase at least one of naphthalene or 2-ethylnaphthalene as the feed with at least one of 1,4-diethylbenzene, 1,2,4-triethylbenzene, at least one tetraethylbenzene or pentaethylbenzene as the ethylating agent at a level of from about 1 to about 10 moles of the ethylating agent per mole of the feed by weight, in the presence of a Lewis acid catalyst selected from the group consisting of aluminum chloride, aluminum bromide, tantalum chloride, antimony fluoride, and red oil, at a level of from about 0.01 to about 1 mole of the catalyst per mole of the feed (for red oil, based on the content of aluminum chloride content of the red oil) by weight and at a temperature in the range of from about $-10°$ C. to about 100° C.

DETAILED DESCRIPTION OF THE PREFERRED EMBODIMENTS

Naphthalene or 2-ethylnaphthalene or mixtures thereof are suitable for use as the feed in the method of this invention. Preferably the feed comprises 2-ethylnaphthalene. As illustrated in the examples hereinbelow, relative to 1,2- and 1,3-diethylbenzenes, 1,2,3- and 1,3,5-triethylbenzenes, and hexaethylbenzene, polyethylated benzenes having from 2, preferably from 3, up to 5 ethyl substituents on the benzene ring, two of which are pra to one another afford substantially improved yields of 2,6- and 2,7-diethylnaphthalenes in the method of this invention. Thus, 1,4-diethylbenzene, 1,2,4-triethylbenzene, any tetraethylbenzene, pentaethylbenzene, and mixtures thereof are the only suitable ethylating agents in the method of this invention. Since all tetraethylbenzenes have at least one pair of ethyl substituents that are in ring positions that are located para to each other, all tetraethylbenzenes are suitable ethylating agents in the method of this invention, and therefore, mixtures of tetraethylbenzene isomers need not be separated and can be used as such as the ethylating agent in the method of this invention. Hexaethylbenzene forms an irreversible addition complex with the acid catalyst and therefore does not work in the preferred method of this invention.

The mole ratio of the ethylating agent-to-naphthalene and/or 2-ethylnaphthalene feed is in the range of from about 1:1, preferably from about 2:1, to about 10:1, preferably to about 5:1, in the method of this invention.

The transethylation reaction of the present invention is conducted in the liquid phase in the presence or absence of a solvent. Any liquid that is inert under the reaction conditions employed and serves as an effective solvent for the reactants and products is suitable for use in the method of this invention. Suitable solvents include halocarbons, such as methylene chloride, chlorobenzene, 1,1-dichloroethane, 1,2-dichloroethane, and chloroform, or carbon disulfide, benzene, cyclohexane, and n-octane. Solvents which are basic and bind irreversibly with the catalyst are not suitable. Such unsuitable solvents include ketones, aldehydes, ethers, esters and alcohols. Preferably the solvent is methylene chloride. If a solvent is employed, the weight of solvent-to-feed compound is in the range of from about 1:1, preferably from about 2:1, to about 15:1, preferably to about 8:1.

Certain specific Lewis acids are suitable for use as the catalyst of the method of this invention. Suitable Lewis acid catalysts include aluminum chloride, aluminum, bromide, tantalum pentachloride, antimony pentafluoride, boron trichloride, and "red oil," a complex polar liquid catalyst phase which is synthesized by addition of ethylchloride or bromide to a slurry of aluminum chloride or some other aforesaid suitable Lewis Acid in an aromatic solvent such as benzene, ethylbenzene, or mixed diethylbenzenes or mixed tetraethylbenzenes. Preferably aluminum chloride is the catalyst. The catalyst can be employed either dissolved in a suitable solvent or in an immiscible phase in a hydrocarbon medium.

Other conventional Lewis acids such as antimony chloride, bismuth chloride, ferric chloride, tin chloride, titanium chloride, zinc chloride and zirconium chloride are not effective catalysts in the preferred method of the present invention. Ethyl bromide and ethyl chloride are useful promoters.

The catalyst is employed in the method of this invention at a level in the range of from abou 0.01, preferably from about 0.05, to about 1.0, preferably to about 0.2 mole per mole of the total of naphthalene and 2-ethylnaphthalene employed.

If the reaction is performed continuously or batchwise, the residence time is from about 0.1, preferably from about 1, to about 10, preferably to about 5 hours.

The reaction temperature is in the range of from about $-10°$ C., preferably from about $-5°$ C., to about $100°$ C., preferably to about $20°$ C. The reaction pressure must be sufficiently high to maintain the reactants and products in the liquid phase at the particular reaction temperature employed, and generally is in the range of from about 0.5, preferably from about 0.8, to about 10, preferably to about 5, atmospheres gauge.

The present invention will be more clearly understood from the following specific examples.

EXAMPLES 1–35

Except as indicated hereinbelow, each of Examples 1–35 was performed using a 250 milliliter, 3-neck round bottom flask equipped with a magnetic stirrer, purged with nitrogen and cooled in an ice bath. The components of the reaction mixture that are identified in Tables 1, 3 and 5 were introduced in the amounts specified in Tables 1, 3 and 5. In each case, the catalyst was introduced last, at which pont the transethylation reaction commenced immediately, and essentially identical reaction conditions were employed in each example. Twenty-four hours after the catalyst was introduced, methanol in a volume that was approximately twice the volume of the reaction medium, was introduced to quench the reaction. The product mixture was then analyzed to determine the combined weight percent of naphthalene (identified as Np in Tables 2, 4 and 6), and 2-ethylnaphthalene (identified as 2-ENp in Tables 2, 4, and 6) that is converted, the combined weight percent of naphthalene and 2-ethylnaphthalene that is converted selectively to 2,6- and 2,7-diethylnaphthalenes (identified as 2,6-DENp and 2,7-DENp, respectively, in Tables 2, 4, and 6) combined, and the relative concentrations of each of 2,6-diethylnaphthalene and 2,7-diethylnaphthalene in the combined amounts of 2,6-diethylnaphthalene and 2,7-diethylnaphthalene produced in each example.

TABLE 1

Amounts[1] of Components Employed in Reaction Mixture

| Example No. | Naphthalene | 2-Ethyl-naphthalene | Aluminum Chloride | Methylene Chloride | 1,4-Diethyl-benzene |
|---|---|---|---|---|---|
| 1 | 6.37 | 6.37 | 1.27 | 25 | 50.94 |
| 2 | 6.37 | 6.37 | 2.54 | 25 | 25.47 |
| 3 | 6.37 | 6.37 | 1.27 | 25 | 38.20 |
| 4 | 6.37 | 6.37 | 2.54 | 25 | |
| 5 | 6.37 | 6.37 | 2.54 | 25 | |
| 6 | 3.82 | 8.91 | 2.54 | 25 | |
| 7 | 3.82 | 8.91 | 2.54 | 25 | |
| 8 | 3.82 | 8.91 | 2.54 | 25 | |
| 9 | 3.82 | 8.91 | 2.54 | 25 | |
| 10 | 3.82 | 8.91 | 1.27 | 10 | |
| 11 | 12.73 | 2.54 | 1.27 | 25 | |
| 12 | 12.73 | | 1.27 | 10 | |
| 13 | 6.37 | 6.37 | 1.27 | 10 | |
| 14 | 3.82 | 8.91 | 1.27 | 25 | |
| 15 | 3.82 | 8.91 | 2.54 | 23 | |
| 16 | 6.37 | 6.37 | 2.54 | 25 | |

| Example No. | 1,3-Diethyl-benzene | 1,2-Ethyl-benzene | 1,2,4-Triethyl-benzene | 1,2-Dimethyl-4-ethyl benzene |
|---|---|---|---|---|
| 1 | | | | |
| 2 | | | | |
| 3 | | | | |
| 4 | 50.94 | | | |
| 5 | | 50.94 | | |
| 6 | | | 38.20 | |
| 7 | | | | 39.48 |
| 8 | | | | |
| 9 | | | | |
| 10 | | | | |
| 11 | | | | |
| 12 | | | | |
| 13 | | | | |
| 14 | | | | |
| 15 | | | | |
| 16 | | | | |

| Example No. | 1,3,5-Tri-ethyl-benzene | Tetra-ethyl-benzene | Penta-ethyl-benzene | Hexa-ethyl-benzene |
|---|---|---|---|---|
| 1 | | | | |
| 2 | | | | |
| 3 | | | | |
| 4 | | | | |
| 5 | | | | |
| 6 | | | | |
| 7 | | | | |
| 8 | 25.47 | | | |

TABLE 1-continued

| Amounts[1] of Components Employed in Reaction Mixture | |
|---|---|
| 9 | 38.20 |
| 10 | 38.20 |
| 11 | 25.47 |
| 12 | 38.20 |
| 13[2] | 38.20 |
| 14[2] | 38.20 |
| 15 | 38.20 |
| 16 | 12.73 |

Footnotes
[1] In millimoles, except in milliliters for methylene chloride
[2] A mixture of 72 weight percent of tetraethylbenzenes and 21 weight percent of pentaethylbenzene.

TABLE 2

| Reaction Time[1] | Conversion[2] of Np + 2-Np | Selectivity[3] to 2,6-DENp | Selectivity[3] to 2,7-DENp | Yield[4] of 2,6-DENp | Yield[4] of 2,7-DENp |
|---|---|---|---|---|---|
| Example 1 | | | | | |
| 30 | 23.6 | 53.5 | 38.2 | 12.63 | 9.02 |
| 60 | 42.4 | 51.6 | 37.5 | 21.88 | 15.90 |
| 120 | 64.0 | 49.4 | 37.7 | 31.62 | 24.13 |
| Example 2 | | | | | |
| 30 | 29.3 | 49.5 | 42.0 | 14.50 | 12.31 |
| 60 | 50.7 | 46.9 | 44.2 | 23.78 | 22.41 |
| 120 | 59.6 | 43.2 | 41.8 | 25.75 | 24.91 |
| Example 3 | | | | | |
| 30 | 26.0 | 52.9 | 39.1 | 13.75 | 10.17 |
| 60 | 40.3 | 51.1 | 39.1 | 20.59 | 15.76 |
| 120 | 54.5 | 49.5 | 38.8 | 26.98 | 21.15 |
| Example 4 | | | | | |
| 30 | 11.4 | 32.5 | 31.6 | 3.71 | 36.02 |
| 60 | 15.3 | 30.3 | 32.3 | 4.64 | 4.94 |
| 120 | 16.6 | 32.7 | 37.2 | 5.43 | 6.18 |
| Example 5 | | | | | |
| 30 | 9.4 | 25.0 | 30.9 | 2.35 | 2.90 |
| 60 | 13.3 | 21.6 | 36.2 | 2.87 | 4.81 |
| 120 | 24.0 | 23.4 | 28.5 | 5.62 | 6.84 |
| Example 6 | | | | | |
| 30 | 55.8 | 61.0 | 30.9 | 34.03 | 17.24 |
| 60 | 67.7 | 57.0 | 31.5 | 38.59 | 21.33 |
| 120 | 80.1 | 50.4 | 30.8 | 40.37 | 24.67 |
| Example 7 | | | | | |
| 30 | 61.5 | 50.1 | 37.9 | 30.81 | 23.31 |
| 60 | 63.1 | 47.5 | 38.1 | 29.97 | 24.04 |
| 120 | 63.4 | 43.9 | 38.0 | 27.83 | 24.09 |
| Example 8 | | | | | |
| 30 | trace | — | — | — | — |
| 60 | 1.3 | 33.1 | 17.5 | 0.43 | 0.23 |
| 120 | 4.7 | 45.8 | 29.1 | 2.15 | 1.37 |
| Example 9 | | | | | |
| 30 | 38.8 | 72.4 | 21.0 | 28.09 | 8.15 |
| 60 | 76.7 | 60.2 | 18.5 | 46.17 | 14.19 |
| 120 | 94.6 | 39.0 | 13.5 | 36.89 | 12.77 |
| Example 10 | | | | | |
| 30 | 7.0 | 77.6 | 21.5 | 5.43 | 1.51 |
| 60 | 23.2 | 75.4 | 20.9 | 17.49 | 4.85 |
| 120 | 71.6 | 63.2 | 19.3 | 45.25 | 13.81 |
| Example 11 | | | | | |
| 30 | 4.6 | 82.3 | 17.7 | 3.79 | 0.81 |
| 60 | 23.9 | 65.3 | 19.0 | 15.61 | 4.54 |
| 120 | 74.3 | 58.0 | 18.9 | 43.09 | 14.04 |
| Example 12 | | | | | |
| 30 | trace | — | — | — | — |
| 60 | 2.9 | 60.4 | 13.1 | 1.75 | 0.38 |
| 120 | 82.3 | 31.4 | 22.8 | 25.84 | 18.76 |
| Example 13 | | | | | |
| 30 | trace | — | — | — | — |
| 60 | 16.9 | 73.7 | 21.3 | 12.45 | 3.60 |
| 120 | 70.4 | 56.5 | 20.0 | 39.78 | 14.08 |
| Example 14 | | | | | |
| 30 | 2.5 | 65.3 | 23.8 | 1.63 | 0.60 |
| 60 | 6.7 | 78.4 | 21.6 | 5.25 | 1.45 |
| 120 | 30.9 | 73.8 | 21.8 | 22.80 | 6.73 |
| Example 15 | | | | | |
| 30 | trace | — | — | — | — |
| 60 | 11.4 | 76.3 | 20.8 | 8.70 | 2.37 |
| 120 | 45.8 | 68.0 | 21.2 | 31.14 | 9.71 |
| Example 16 | | | | | |
| 30 | trace | — | — | — | — |
| 60 | trace | — | — | — | — |
| 120 | trace | — | — | — | — |

Footnotes
[1] Minutes
[2] Weight percent of feed compound converted
[3] Weight percent of feed compound converted that is converted to 2,6- or 2,7-DENp
[4] Product of conversion and selectivity to 2,6- or 2,7-DENp

TABLE 3

| Example No. | Naphthalene | 2-Ethylnaphthalene | 1,4-Diethylbenzene | Tetraethylbenzene | Methylene Chloride |
|---|---|---|---|---|---|
| 17 | 6.37 | 6.37 | 25.47 | | 25[2] |
| 18 | 6.37 | 6.37 | 25.47 | | 25[3] |
| 19 | 6.37 | 6.37 | 25.47 | | 25 |
| 20 | 6.37 | 6.37 | 25.47 | | 25 |
| 21 | 6.37 | 6.37 | 25.47 | | 25 |
| 22 | 6.37 | 6.37 | 25.47 | | 25 |
| 23 | 6.37 | 6.37 | 25.47 | | 25 |
| 24 | 6.37 | 6.37 | 25.47 | | 25 |
| 25 | 6.37 | 6.37 | 25.47 | | 25 |
| 26 | 6.37 | 6.37 | 25.47 | | 25 |
| 27 | 6.37 | 6.37 | 25.47 | | 25 |
| 28 | 3.82 | 8.91 | 38.20 | | 25 |
| 29 | 12.73 | | | 38.20 | 10 |
| 30 | 12.73 | | | 38.20 | 10[3] |
| 31 | 12.73 | 12.73 | | 76.40 | |

| Example No. | Aluminum Bromide | Tantalum Chloride | Zinc Chloride | Stannic Chloride | Titanium Chloride |
|---|---|---|---|---|---|
| 17 | 2.54 | | | | |
| 18 | 6.37 | | | | |
| 19 | | 2.54 | | | |
| 20 | | | 2.54 | | |
| 21 | | | | 2.54 | |
| 22 | | | | | 2.54 |
| 23 | | | | | |
| 24 | | | | | |
| 25 | | | | | |
| 26 | | | | | |
| 27 | | | | | |
| 28 | | | | | |
| 29 | | | | | |
| 30 | | | | | |
| 31 | | | | | |

| Example No. | Antimony Chloride | Antimony Fluoride | Ferric Chloride | Bismuth Chloride | Zirconium Chloride | Red[5] Oil |
|---|---|---|---|---|---|---|
| 17 | | | | | | |
| 18 | | | | | | |
| 19 | | | | | | |
| 20 | | | | | | |
| 21 | | | | | | |
| 22 | | | | | | |
| 23 | 2.54 | | | | | |
| 24 | | 3.57 | | | | |
| 25 | | | 8.27 | | | |
| 26 | | | 12.73 | | | |
| 27 | | | | 2.54 | | |
| 28 | | | | | 1.27 | |
| 29 | | | | | | 2.54[4] |
| 30 | | | | | | 2.54[4] |
| 31 | | | | | | 2.54[4] |

Footnotes
[1] In millimoles, except in milliliters for methylene chloride
[2] Carbon disulfide instead of methylene chloride
[3] Benzene instead of methylene chloride
[4] Contains additionally 2.45-3.81 millimoles of ethyl bromide as a promoter
[5] Millimoles of aluminum chloride in red oil

TABLE 4

| Reaction Time[1] | Conversion[2] of Np + 2-Np | Selectivity[3] to 2,6-DENp | Selectivity[3] to 2,7-DENp | Yield[4] of 2,6-DENp | Yield[4] of 2,7-DENp |
|---|---|---|---|---|---|
| Example 17 | | | | | |
| 30 | 5.2 | 70.5 | 29.5 | 3.67 | 1.53 |
| 60 | 17.5 | 63.9 | 36.1 | 11.18 | 6.32 |
| 120 | 38.5 | 53.2 | 44.4 | 20.48 | 17.09 |
| 240 | 57.8 | 40.1 | 40.7 | 23.18 | 23.52 |
| Example 18 | | | | | |
| 30 | 14.5 | 45.8 | 42.4 | 6.64 | 6.14 |
| 60 | 20.8 | 42.6 | 45.0 | 8.86 | 9.36 |
| 120 | 36.1 | 33.4 | 47.5 | 12.06 | 17.15 |
| Example 19 | | | | | |
| 30 | 25.1 | 42.9 | 25.2 | 10.77 | 6.33 |
| 60 | 35.8 | 41.6 | 27.0 | 14.89 | 9.67 |
| 120 | 45.3 | 42.6 | 31.7 | 19.30 | 14.36 |
| Example 20 | | | | | |
| 30 | trace | — | — | — | — |
| 60 | trace | — | — | — | — |
| 120 | trace | — | — | — | — |
| Example 21 | | | | | |
| 30 | trace | — | — | — | — |
| 60 | trace | — | — | — | — |
| 120 | trace | — | — | — | — |
| Example 22 | | | | | |
| 30 | trace | — | — | — | — |
| 60 | trace | — | — | — | — |
| 120 | trace | — | — | — | — |
| Example 23 | | | | | |
| 30 | trace | — | — | — | — |
| 60 | trace | — | — | — | — |
| 120 | trace | — | — | — | — |
| Example 24 | | | | | |
| 30 | 28.8 | 52.9 | 43.0 | 15.24 | 12.38 |
| 60 | 39.0 | 49.6 | 41.7 | 19.34 | 16.26 |
| 120 | 44.8 | 46.6 | 42.4 | 20.88 | 19.00 |
| Example 25 | | | | | |
| 30 | trace | — | — | — | — |
| 60 | trace | — | — | — | — |
| 120 | trace | — | — | — | — |
| Example 26 | | | | | |
| 30 | trace | — | — | — | — |
| 60 | trace | — | — | — | — |
| 120 | trace | — | — | — | — |
| Example 27 | | | | | |
| 30 | trace | — | — | — | — |
| 60 | trace | — | — | — | — |
| 120 | trace | — | — | — | — |
| Example 28 | | | | | |
| 30 | trace | — | — | — | — |
| 60 | trace | — | — | — | — |
| 120 | trace | — | — | — | — |
| Example 29 | | | | | |
| 30 | 1.4 | 53.8 | 12.8 | 0.75 | 0.18 |
| 60 | 3.3 | 75.6 | 19.2 | 2.49 | 0.63 |
| 120 | 17.5 | 73.9 | 21.8 | 12.93 | 3.81 |
| 180 | 86.3 | 45.5 | 20.3 | 39.27 | 17.52 |
| Example 30 | | | | | |
| 30 | trace | — | — | — | — |
| 60 | trace | — | — | — | — |
| 120 | 2.1 | 75.6 | 16.6 | 1.59 | 0.35 |
| 240 | 29.7 | 65.6 | 25.0 | 19.48 | 0.74 |
| 1440 | 89.6 | 34.1 | 23.7 | 30.55 | 21.24 |
| Example 31 | | | | | |
| 30 | 1.4 | 79.4 | 18.6 | 1.11 | 0.26 |
| 60 | 4.8 | 81.2 | 18.8 | 3.90 | 0.90 |
| 120 | 18.2 | 77.6 | 19.6 | 14.12 | 3.57 |
| 240 | 42.7 | 71.5 | 21.5 | 30.53 | 9.18 |
| 360 | 55.7 | 65.4 | 21.2 | 36.43 | 11.81 |

Footnotes
[1] Minutes
[2] Weight percent of feed compound converted
[3] Weight percent of feed compound converted that is converted to 2,6- or 2,7-DENp
[4] Product of conversion and selectivity to 2,6- or 2,7-DENp

TABLE 5

Amounts[1] of Components Employed in Reaction Mixture

| Example No. | Naphthalene | 2-Ethyl-naphthalene | 1,4-Di-ethylbenzene | Tetra-ethylbenzene | Aluminum Chloride |
|---|---|---|---|---|---|
| 17 | 6.37 | 6.37 | 25.47 | | |
| 18 | 6.37 | 6.37 | 25.47 | | |
| 32 | 6.37 | 6.37 | 25.47 | | 1.27 |
| 33 | 12.73 | | | 38.20 | 1.27 |
| 34 | 12.73 | | | 38.20 | 1.27 |

| Example No. | Aluminum Bromide | Carbon Disulfide | Benzene | Chlorobenzene | 1,2-Dichloroethane | 1,2-Dichloroform |
|---|---|---|---|---|---|---|
| 17 | 2.54 | 25 | | | | |
| 18 | 6.37 | | | 25 | | |
| 32 | | | | | 25 | |
| 33 | | | | | 25 | |
| 34 | | | | | | 10 |

Footnotes
[1] In millimoles, except in milliliters for methylene chloride

TABLE 6

| Reaction Time[1] | Conversion[2] of Np + 2-Np | Selectivity[3] to 2,6-DENp | Selectivity[3] to 2,7-DENp | Yield[4] of 2,6-DENp | Yield[4] of 2,7-DENp |
|---|---|---|---|---|---|
| Example 17 | | | | | |
| 30 | 5.2 | 70.5 | 29.5 | 3.67 | 1.53 |
| 60 | 17.5 | 63.9 | 36.1 | 11.18 | 6.32 |
| 120 | 38.5 | 53.2 | 44.4 | 20.48 | 17.09 |
| Example 18 | | | | | |
| 30 | 14.5 | 45.8 | 42.4 | 6.64 | 6.15 |
| 60 | 20.8 | 42.6 | 45.0 | 8.86 | 9.36 |
| 120 | 36.1 | 33.4 | 47.5 | 12.06 | 17.15 |
| Example 32 | | | | | |
| 30 | 37.0 | 47.8 | 42.0 | 17.69 | 15.54 |
| 60 | 47.8 | 45.4 | 40.7 | 21.70 | 19.45 |
| 90 | 51.8 | 43.1 | 40.3 | 22.33 | 20.88 |
| Example 33 | | | | | |
| 30 | 13.2 | 60.4 | 26.6 | 7.97 | 2.72 |
| 60 | 42.7 | 60.6 | 23.6 | 25.88 | 10.08 |
| 90 | 78.9 | 48.8 | 22.2 | 38.50 | 17.52 |
| Example 34 | | | | | |
| 30 | trace 0 | — | — | — | — |
| 60 | trace 0 | — | — | — | — |
| 90 | 64.5 | 48.3 | 18.2 | 31.15 | 18.26 |
| Example 35 | | | | | |

Footnotes
[1] Minutes
[2] Wt. % of feed compound conv.
[3] Wt. % of feed compound conv. that is converted to 2,6- or 2,7-DENp
[4] Product of conv. & select. to 2,6- or 2,7-DENp Comparison of the results from Examples 1–16, 32 and 33 illustrates that the superiority of tetra- and pentaethylbenzenes as selective ethylating agents and the superiority within the same compound class of p-substituted isomers over their non-parasubstituted isomers. Comparison of the results from Examples 1–3 illustrates that the effect of the ratio of ethylating agent-to-feedstock compounds on activity, with higher such ratios affording higher activity and reaction rates. Comparison of the results from Examples 9–12 illustrates (1) higher catalytic activity at higher catalyst loadings but with little change in selectivity and (2) higher selectivity and yield with 2-ethylnaphthalene present in the feed. Comparison of the results from Examples 13–14 illustrates that a mixture of tetraethylbenzenes prepared by the ethylation of a lower ethylbenzene with ethylene is a suitable ethylating agent for the selective production of 2,6-diethylnaphthalene.

Example 15 illustrates that pentaethylbenzene, like tetraethylbenzenes, is a highly selective ethylating agent in the method of the present invention. Comparison of the results from Examples 17-31 illustrates that Lewis acids that are at least as acidic as aluminum chloride exhibit significant activity for the production of 2,6-diethylnaphthalene. Comparison of the results from Examples 17-18 illustrates that soluble catalysts in nonpolar solvents are effective in the method of this invention for the production of 2,6-diethylnaphthalene. The results of Examples 19 and 24 illustrate that tantalum, pentachloride and antimony pentafluoride, although less active than aluminum chloride, are more selective than aluminum chloride and afford high ratios of 2,6- to 2,7-diethylnaphthalene.

Comparison of the results from Examples 25-28 illustrates that ferric chloride, bismuth chloride and zirconium chloride are inactive under the reaction conditions employed. Comparison of the results from Examples 29-31 illustrates that "red oil"—complexes of aluminum chloride with an alkyl halide (or with hydrogen chloride and an olefin) and an aromatic compound are highly selective catalysts in the present invention.

Examples 17, 18, 29-31 and 32-35 illustrate that the method of the present invention can be carried out as either (1) a homogeneous catalytic reaction in a solvent in which both the catalyst and reactants are dissolved or (2) a heterogeneous catalytic reaction with either a nonpolar solvent or no solvent, in which case the catalyst comprises a polar liquid phase—for example red oil—which exhibits little or no solubility for the reactants.

From the above description, it is apparent that the objects of the present invention have been achieved. While only certain embodiments have been set forth, alternative embodiments and various modifications will be apparent from the above description to those skilled in the art. These alternatives are considered equivalents and within the spirit and scope of the present invention.

Having described the invention, what is claimed is:

1. A method for producing 2,6-diethylnaphthalene, comprising: reacting in the liquid phase at least one of naphthalene or 2-ethylnaphthalene as the feed with at least one of 1,2,4-triethylbenzene, at least one tetraethylbenzene or pentaethylbenzene as the ethylating agent at a level of from about 1 to about 10 moles of the ethylating agent per mole of the feed by weight, in the presence of a Lewis acid catalyst selected from the group consisting of aluminum chloride, aluminum bromide, boron trichloride, tantalum pentachloride, antimony pentafluoride, and red oil, at a level of from about 0.01 to about 1 mole of the catalyst per mole of the feed by weight and at a temperature in the range of from about $-10°$ C. to about $100°$ C.

2. The method of claim 1 wherein the feed comprises 2-ethylnaphthalene.

3. The method of claim 1 wherein the ethylating agent is a tetraethylbenzene, pentaethylbenzene or a mixture thereof.

4. The method of claim 1 wherein the ethylating agent is at a level of from about 2 to about 5 moles per mole of the feed by weight.

5. The method of claim 1 wherein the Lewis acid catalyst comprises aluminum chloride.

6. The method of claim 1 wherein the Lewis acid catalyst comprises red oil.

7. The method of claim 1 wherein the Lewis acid is at a level of from 0.05 to about 0.2 mole per mole of the feed by weight.

8. The method of claim 1 wherein the Lewis acid is employed as dissolved in a solvent comprising methylene chloride or chlorobenzene.

9. The method of claim 8 wherein the solvent comprises any hydrocarbon or halocarbon.

10. The metho of claim 1 wherein the feed and ethylating agent are dissolved in a solvent comprising a halocarbon, carbon disulfide, benzene, cyclohexane or n-octane.

11. The method of claim 1 wherein the reaction is conducted at a temperature in the range of from about $-5°$ C. to about $20°$ C.

* * * * *

UNITED STATES PATENT OFFICE
CERTIFICATE OF CORRECTION

Patent No. 4,873,386     Dated October 10, 1989

Inventor(s) Gary P. Hagen and Thomas E. Nemo

It is certified that error appears in the above-identified patent and that said Letters Patent is hereby corrected as shown below:

| Col. | Line | |
|---|---|---|
| 2 | 4 | "≧" should read -->-- (second occurrence) |
| 2 | 56 | "pra" should read --para-- |
| 4 | 4 | "pont" should read --point-- |
| 6 | 66 | "2.45" should read --2.54-- |
| 9 | 6 | "cataysts" should read --catalysts-- |
| 10 | 33 | "metho" should read --method-- |

Signed and Sealed this

Thirtieth Day of October, 1990

Attest:

HARRY F. MANBECK, JR.

Attesting Officer     Commissioner of Patents and Trademarks